US006988930B2

(12) United States Patent
Gillan

(10) Patent No.: US 6,988,930 B2
(45) Date of Patent: Jan. 24, 2006

(54) HANDS-FREE BREAST MILK EXPRESSION SYSTEM

(76) Inventor: Jonathan C. Gillan, 306 E. 15th St., Tempe, AZ (US) 85281

( * ) Notice: Subject to any disclaimer, the term of this patent is extended or adjusted under 35 U.S.C. 154(b) by 0 days.

(21) Appl. No.: 10/895,032

(22) Filed: Jul. 19, 2004

(65) Prior Publication Data

US 2005/0112995 A1    May 26, 2005

Related U.S. Application Data

(63) Continuation of application No. 10/143,326, filed on May 9, 2002, now Pat. No. 6,764,377.

(51) Int. Cl.
*A41C 3/00* (2006.01)

(52) U.S. Cl. .............................. 450/36; 604/74; 2/104

(58) Field of Classification Search ................. 450/36, 450/37; 2/104; 604/118, 119, 73–76, 315, 604/320, 322, 323, 326, 346; 601/14, 6; 128/890; 54/20, 58, 59; 119/14.43, 14.47, 119/14.48, 14.49, 14.51
See application file for complete search history.

(56) References Cited

U.S. PATENT DOCUMENTS

| | | | | |
|---|---|---|---|---|
| 949,414 A | * | 2/1910 | Cunningham | 604/76 |
| 4,584,992 A | * | 4/1986 | Liu | 601/14 |
| 4,857,051 A | * | 8/1989 | Larsson | 604/74 |
| 5,415,632 A | * | 5/1995 | Samson | 604/74 |
| 5,575,768 A | * | 11/1996 | Lockridge et al. | 604/74 |
| 5,616,125 A | * | 4/1997 | Jelks | 604/74 |
| 6,004,186 A | * | 12/1999 | Penny | 450/36 |
| 6,213,840 B1 | * | 4/2001 | Han | 450/36 |
| 6,247,996 B1 | * | 6/2001 | Fields | 450/36 |

* cited by examiner

*Primary Examiner*—Gloria M. Hale
(74) *Attorney, Agent, or Firm*—Louis J. Hoffman; Edwin A. Suominen

(57) ABSTRACT

A disclosed breast milk expression system supports a pair of breast milk collection devices at the breasts of a nursing mother, allowing her to express breast milk while keeping her hands free. No special bra or other garment is required to provide support. The system includes a substantially rigid bar, a strap, and a pair of breast milk collection device connectors at or near opposite ends of the bar. The strap is comprised of a length of slender, flexible support material, significantly longer than the bar. The strap extends from a point at or near one end of the bar to a point at or near another end of the bar and can suspend from a nursing mother's neck, thereby suspending a pair of breast milk collection devices near the nursing mother's breasts to express milk from them. Numerous variations and methods are also disclosed.

19 Claims, 4 Drawing Sheets

HANDS-FREE BREAST MILK EXPRESSION SYSTEM

CROSS REFERENCE TO RELATED APPLICATIONS

This application is a continuation of application Ser. No. 10/143,326 filed May 9, 2002, now U.S. Pat. No. 6,764,377.

BACKGROUND OF THE INVENTION

Nursing mothers who express their breast milk for later use often find themselves inconvenienced by the need to support a breast milk collection device with their hands while it operates. (As used herein, the term "breast milk collection device" refers to any apparatus suitable for collecting expressed breast milk, e.g., an assembly that includes a suction cup, receiving tube, Venturi channel, and milk bottle.) Attempting to "double pump" typically requires both hands, one for a collection device at each breast, which leaves a nursing mother with little way to accomplish any other tasks or even read during the lengthy process.

Various "hands free" breast pumping arrangements have been developed, but they are far from being ideal solutions to the problem. For example, the system disclosed in U.S. Pat. No. 6,247,996 to Fields requires the user to wear a special bra that serves as a support harness for the collection devices. For a manufacturer of breast pumping devices to provide such a specially designed undergarment raises challenges, especially since women wear bras of many different styles and sizes. Typically, women purchase bras in a retail store environment where they can ensure a correct fit and select the style that appeals to them, often with the assistance of trained sales personnel. They may not be eager to purchase such a personal item of clothing from an equipment manufacturer, especially without having the opportunity to try it on beforehand.

Accordingly, nursing mothers still need a convenient, effective, hands-free way to support one or two breast milk collection devices while expressing milk, without resorting to any garment or undergarment other than what they would ordinarily wear.

SUMMARY OF THE INVENTION

A breast milk expression system according to various aspects of the present invention conveniently and effectively supports a pair of breast milk collection devices at the breasts of a nursing mother, allowing her to express breast milk while keeping her hands free for other tasks. Advantageously, no special bra or other garment is required to provide support for the collection devices. The system includes a bar, a strap, and a pair of breast milk collection device connectors. The bar is comprised of a length of substantially rigid material, embodied in one or several distinct structures fabricated from such material, which connects two points on the material. Each connector secures to the bar near a respective one of these points.

The strap is comprised of a length of slender, flexible support material. The length of strap material is significantly greater than the length of the bar material. The strap is secured to the bar, with a point at or near each end of the strap connected to a point at or near each end of the bar. This arrangement permits the holder to form a loop from one end of the bar to the other. Advantageously, the strap can suspend from a nursing mother's neck, thereby suspending the breast milk collection devices near the nursing mother's breasts to express milk from them.

According to a more particular aspect of the invention, the pair of connectors can include a pair of releasable retaining structures. Each of these structures can releasably secure a breast milk collection device to the bar. In a particularly advantageous configuration, the structures each include a J-shaped hook comprised of a length of slender, substantially rigid material. The hook has an arc that is approximately or exactly semicircular and first and second straight portions that are parallel to each other and at opposite ends of the arc. Each structure further includes a cap, of size comparable to an average human thumb width, that has in one of its sides a recess of suitable size to receive an end part of the first straight portion. Further included in each of the structures is a compression spring sized to fit over the first straight portion.

The first straight portion of the hook passes through a first hole in the bar, through the spring, and into the recess of the cap. The second straight portion of the hook is shorter than the first and passes through a second hole in the bar. In this configuration, simple thumb pressure on the cap can release the hook's shorter second straight portion from the bar's second hole, freeing the longer first straight portion to swivel in the bar's first hole. Thus, an intuitive and straightforward release mechanism is provided.

The above summary does not include an exhaustive list of all aspects of the present invention. Indeed, the inventor contemplates that the invention includes all systems and methods that can be practiced from all suitable combinations of the various aspects summarized above, as well as those disclosed in the detailed description below and particularly pointed out in the claims filed with the application. Such combinations have particular advantages not specifically recited in the above summary.

BRIEF DESCRIPTION OF THE DRAWINGS

Various embodiments of the present invention are described below with reference to the drawings, wherein like designations denote like elements.

DESCRIPTION OF PREFERRED EXEMPLARY EMBODIMENTS

Figure 1:
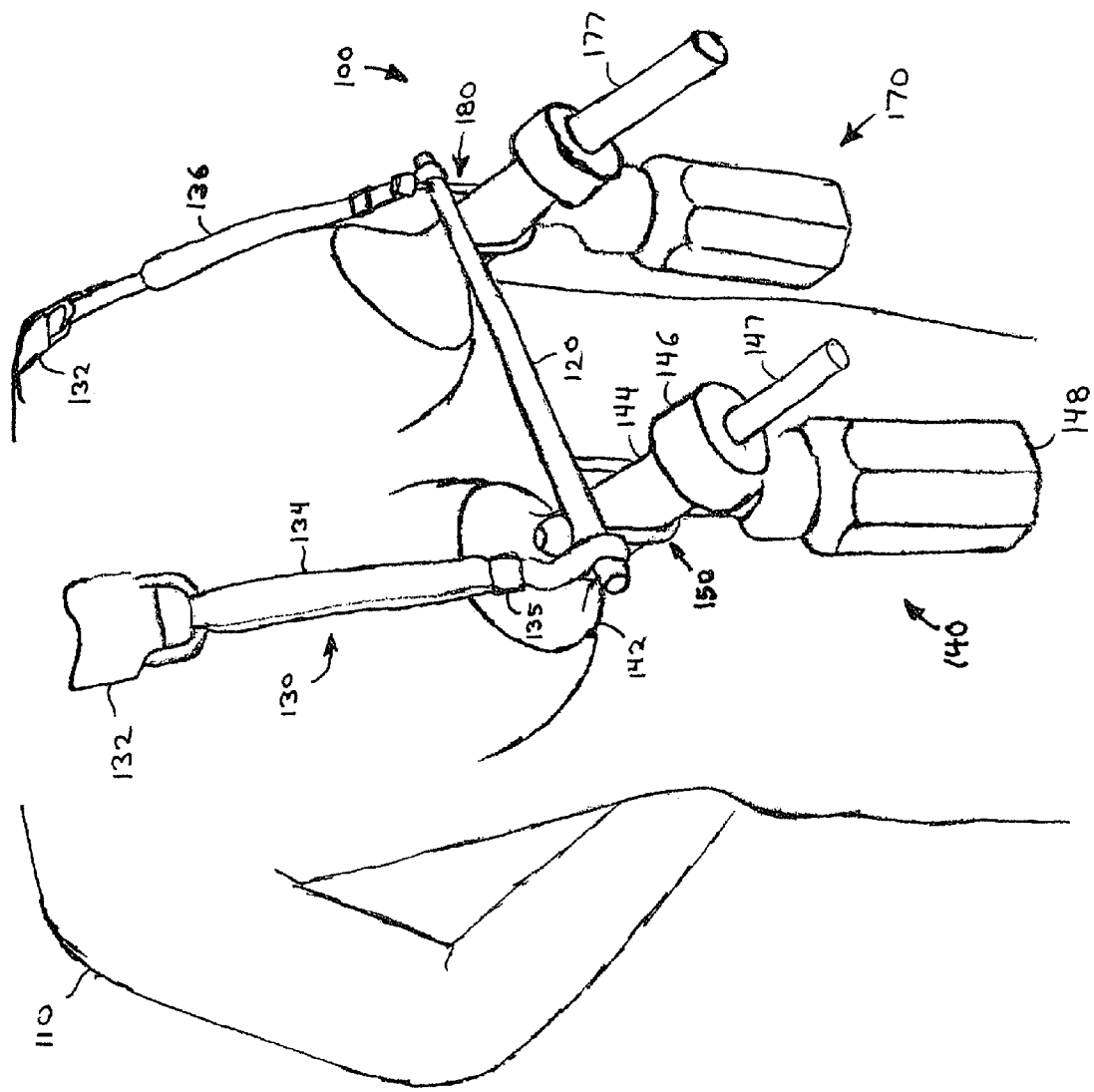
FIG. 1 is a perspective view of a pair of breast milk collection devices suspended, in accordance with various aspects of the invention, near a nursing mother's breasts by a bar and a neck-worn strap.

A breast milk expression system according to various aspects of the present invention provides numerous benefits, notably the facilitation of hands-free "double pumping" without the need for any special bra or other garment. An advantageous combination of a substantially rigid bar and a flexible strap support a pair of breast milk collection devices near a nursing mother's breasts to express milk from the breasts. As may be better understood with reference to FIG. 1, for example, one such system 100 includes: a strap 130 comprised of strap material that suspends from the neck (not shown) of a wearer 110 (a nursing mother); a bar 120 connected to strap 130; and a pair of breast milk collection devices 140, 170 that suspend from bar 120 via connectors 150, 180, respectively. Devices 140, 170 circulate air with an external pumping device (not shown) via hoses 147, 177 to develop suction conventionally by the Venturi effect, as discussed below.

Suspension of collection devices 140, 170 from the neck of wearer 110 contributes to the effectiveness of breast milk expression as well as making the process a more convenient one. In exemplary system 100, strap 130 suspends from a single support point and imparts forces at two separated points along bar 120. These forces have upward components and partially opposing horizontal components. Rigidity of bar 120 neutralizes the opposing vectors of the horizontal components, and the remaining horizontal vectors direct force toward the chest of wearer 110. This force, along with suction from the milk expression process, helps keep breast milk collection devices 140, 170 firmly in contact with breasts of wearer 110. Neutralization of perpendicular forces by bar 120 helps prevent devices 140, 170 from being dislodged, e.g., by twisting moment of hoses 147, 177 during pumping action.

In a variation of strap 130 having more distributed support, e.g., a bra-type cross-strap about the shoulders that perhaps does not even touch the neck, the opposing vectors of the horizontal components may be diminished. But vectors of substantially similar magnitude pointing toward the chest of wearer 110 can be expected to remain, providing the advantageous contact-maintaining force described above.

Two important dimensions of exemplary system 100 are adjustable to advantageously suspend collection devices 140, 170 near the breasts of wearer 110 regardless of her body dimensions. First, wearer 110 can adjust the length of strap 130 to raise or lower devices 140, 170. Second, she can accommodate her chest width by adjusting the length of bar 120 between two points on the bar, near which collection devices 140, 170 are attached. The flexible positioning offered by these adjustments allows system 100 to accommodate a significant majority of nursing mother's bodies in a given population of interest, a population that may be more specifically defined for marketing to a particular region or more generally defined for worldwide marketing.

A strap according to various aspects of the invention includes any length of slender, flexible support material suitable for suspending a modest load around a person's neck. For example, the support material can have a cross section that is thin and flat (e.g., a camera strap) or round (e.g., a braided soft-core cord). As illustrated in FIG. 1, strap 130 is flat, having a central portion of its length of support material that is comprised of a wide, padded strap 132 and two end portions 134, 136 comprised of narrower, thinner straps (e.g., of nylon webbing).

To position collection devices 140, 170 at a suitable position below her neckline, wearer 110 can conventionally adjust the length of strap 130 by sliding a clip 135 up or down along the loop of end portion 134. The position of clip 135 determines the amount of doubled-up strap present, which influences overall length of strap 130. End portion 136 is amenable to the same type of adjustment, permitting further variation in the overall length of strap 130.

A breast milk expression system according to various aspects of the invention can use a suitable length of any substantially rigid as a bar to separate two points on the material's length near which breast milk collection devices can attach. (These "points" are merely identifications of geometrical positions on structure and do not necessarily embody any separate structure themselves.) The length of material can comprise a single rigid structure or several rigid structures connected together.

Figure 2:
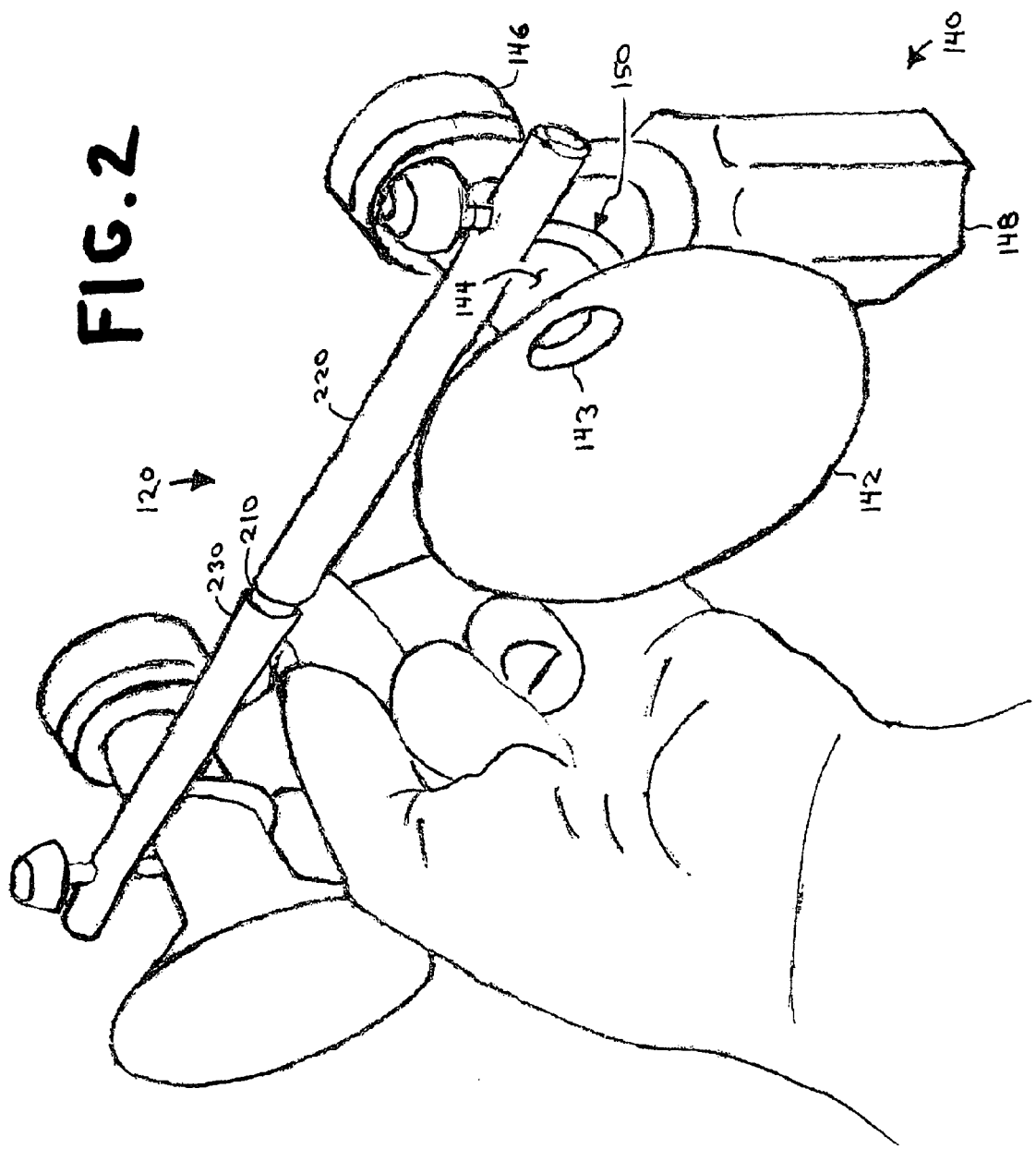
FIG. 2 is a perspective view of the breast milk collection devices and bar of FIG. 1 supported by a person's index finger, illustrating the light weight and balance that an embodiment of the invention can achieve.
Figure 3:
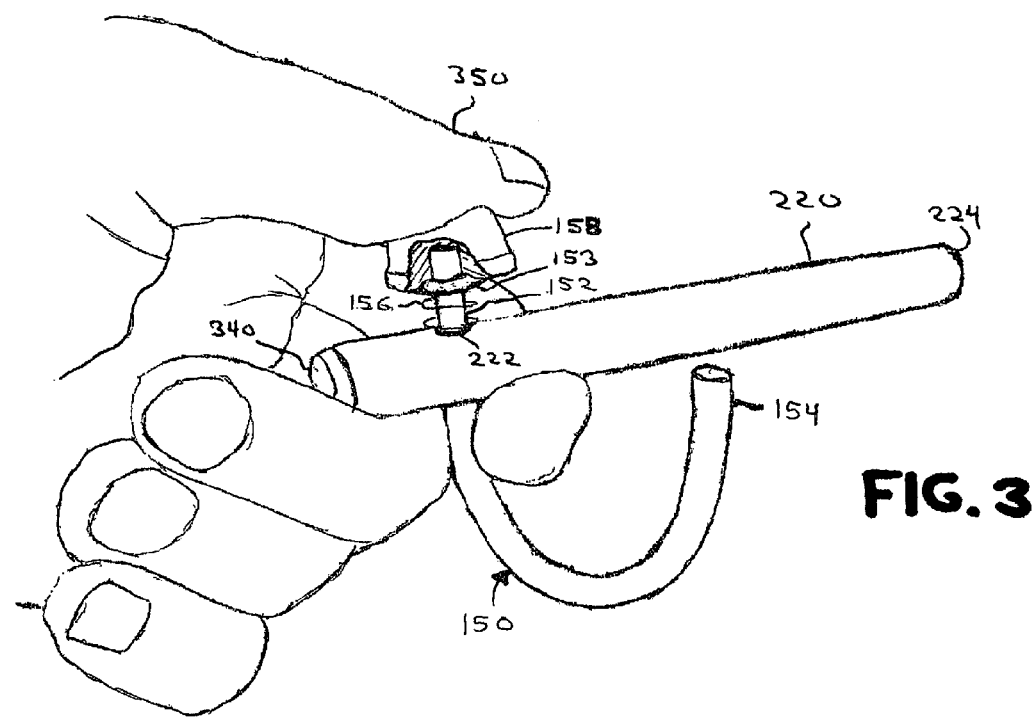
FIG. 3 is a perspective view of a sleeve portion of the bar of FIGS. 1–2 and a connector that couples one of the breast milk collection devices of FIG. 1 to the bar.
Figure 4:
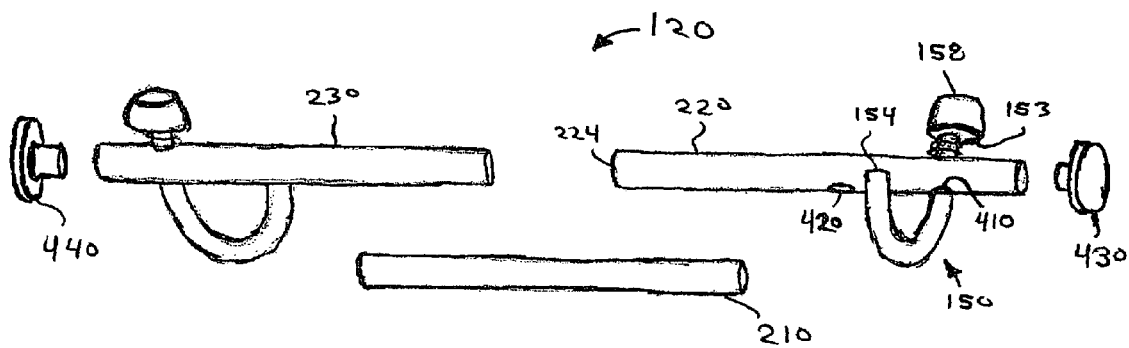
FIG. 4 is an exploded view of the bar of FIGS. 1–2 illustrating a central rod and two sleeve portions that receive the rod.

As may be better understood with reference to FIGS. 2–4, bar 120 of exemplary system 100 includes a central rod 210 and a pair of sleeve portions 220, 230 (FIG. 2) that fit snugly onto rod 210. Sleeve portions 220, 230 have hollow interiors that are each dimensioned and shaped to receive a portion of rod 210 from one of its ends to a point at or near its center. For example, sleeve portion 220 is essentially a cylinder of thin-walled metal (stainless steel is preferred, as discussed below) with an opening 224 (FIG. 4) having an inside diameter only slightly larger (e.g., by 0.9 mm) than the outside diameter of rod 210, which is preferably also stainless steel and can be hollow.

In this exemplary configuration, friction between the exterior surface of rod 210 and the interior surface of sleeve portion 220 maintains the relative position between the two structures under normal conditions of use but permits wearer 110 to adjust their position by gently pushing them together or pulling them apart. To help ensure stability, the end of each sleeve 220, 230 preferably overlaps its respective end of rod 210 by at least about half an inch.

In a somewhat less versatile variation of bar 120, rod 210 is rigidly mounted within one of sleeve portions 220, 230, leaving length adjustment to the sliding interconnection between rod 210 and the other sleeve portion.

A few examples of substantially rigid materials that a bar such as bar 120 can employ include ABS plastic, wood, stainless steel, and anodized aluminum. Rigidity can come from the inherent stiffness of the material, its structural configuration (e.g., a hollow-core tube), or a combination of both. Stainless steel has several advantages that make it a preferred choice as a material, including visual appeal, strength, and corrosion resistance that makes it suitable for washing. The entire length of substantially rigid material in a bar need not comprise a single type of such material. For example, rod 210 can be fabricated from solid ABS plastic while sleeve portions 220, 230 can be fabricated from stainless steel.

As discussed above, strap 130 and bar 120 adjust in length using sliding clip 135 of FIG. 1 (and a counterpart clip for strap portion 136, not shown in FIG. 1) and the slidable connection of rod 210 and sleeve portions 220, 230. However, a bar and strap according to various aspects of the invention can employ any suitable structural arrangement to permit length adjustment. A few examples are listed as follows.

ADJUSTMENT EXAMPLE 1—the bar consists of two thin, flat sections of hard rubber. One section contains a number of receiving holes lined up across much of the section's length. The other section contains a number of raised bumps, one for each receiving hole, that are similarly lined up across that section's length. The two sections releasably connect together by engagement of some or all the bumps into or through respective receiving holes, with the length of the resulting bar dependent on how many of the bumps are engaged, similar to length adjustment of a baseball cap's back strap. The bumps can be slightly protruding portions of a continuous segment of hard rubber making up the bar. In one possible variation, the "bumps" can be individual structures connected to the main bar material by compression springs.

ADJUSTMENT EXAMPLE 2—the strap is made up of two sections of string, preferably flat like an apron string or including a padded wrapper along at least a portion of its length to ease contact with the wearer's neck. The string sections are simply tied together in a bow, with the amount of leftover string in and beyond the bow knot determining the strap length.

ADJUSTMENT EXAMPLE 3—the bar is comprised of two thin, flat strips of steel. Each strip has a "keeper" band fixedly mounted at one end. The keeper band is a band of rigid material, e.g., steel, with four straight sides and a rectangular cross-section. The length of the cross-section is substantially the same as the width of the bar, and one of the band's sides adhesively secures to the end of the strip to which it is attached. The other strip can then pass through the remaining part within the band's cross-section, which is made small enough to provide some friction between the bar and the band. As a result, the two strips can slide back and forth with respect to each other when force is applied to them, but they remain stable at a given position otherwise.

ADJUSTMENT EXAMPLE 4—the bar is a single piece of substantially rigid material, e.g., neoprene, that has multiple slots symmetrically disposed about its center. Each slot is oriented perpendicular to the bar's lengthwise axis. Each of a pair of breast milk collection devices releasably secures to the bar by a clip or tab that fits through one of the slots. As mentioned above, a bar according to various aspects of the invention is comprised of a length of substantially rigid material separating two points on the material. In this example, those points are located at the two selected slots. Thus, the length of substantially rigid material separating the two points is less than the total length of material in the bar. Here, the "length of material" is adjusted by selecting different points of separation at which the collection devices are attached (which define the length in question), not by changing the length of the bar itself.

A breast milk collection device according to various aspects of the invention includes any structure suitable for coupling to a lactating human breast to express and collect milk. For example, device 140 of FIGS. 1–2 includes a suction cup 142 (e.g., of semi-transparent rigid neoprene) that is dimensioned and shaped to receive a portion of a breast of wearer 110, and that includes a central opening 143 (FIG. 2). Device 140 further includes: a receiving tube 144 in fluid communication with the interior of suction cup 142 through central opening 143; a milk bottle 148; and a Venturi channel 146.

Air is directed from an external pumping device (not shown) to Venturi channel 146 and back again to the pumping device via a hose 147, which contains forward and reverse air (also not shown) inside hose 147. Venturi channel 146 is shaped internally to develop suction in receiving tube 144 as a result of that air flow, in accordance with the Venturi effect.

Device 140 may be of any suitable type. Examples include the device disclosed in U.S. Pat. No. 4,857,051 to Larsson (the detailed description portion of which is incorporated herein by reference), the devices marketed by Medela, Inc. of McHenry, Ill. with the "Pump in Style" dual breast pump kit, and the devices marketed by Ameda Breastfeeding Products (Hollister Inc.) of Libertyville, Ill.

Breast milk collection device 140 connects to bar 120 via a breast milk collection device connector 150. Similarly, collection device 170 connects to bar 120 via a like connector 180. Exemplary connectors 150 and 180 are releasable retaining structures. A releasable retaining structure according to various aspects of the invention includes any configuration of mechanical elements that, when desired, can fasten to a bar and retain a portion of a breast milk collection device to the bar and, when desired, can release itself and the collection device from the bar. Retaining structure of connector 150 may be better understood with reference to FIGS. 3–5.

FIG. 3 illustrates connector 150 mounted to sleeve portion 220 of bar 120 in an open (i.e., released) configuration. That configuration is maintained by pressure from a person's thumb 350, as discussed below. Structure 150 includes a hook comprised of a length of slender, substantially rigid material (i.e., any type of material that may be used in bar 120), preferably stainless steel. The material curves in an arc that is approximately or exactly semicircular, terminating in straight portions 152, 154 (FIG. 3) that extend beyond the semicircular portion of the arc. Straight portion 152 is longer than straight portion 154, an asymmetry that permits portion 152 to extend completely through a top hole 222 and a bottom hole 410 (FIG. 4) in sleeve portion 220 while portion 154 extends only partially inside sleeve portion 220, through a single bottom hole 420.

Portion 152 extends above sleeve portion 220 a short distance to its end. A cap 158 receives the end of portion 152 in a recess (depicted in the cutaway view of cap 158) in its bottom side. Preferably, the recess of cap 158 includes conventional barbs about its circumference to secure the end of portion 152 in place.

A compression spring 156 fits over the short length of end portion 152 between hole 222 and a preferably stainless steel washer 153 (FIGS. 3–4) adjacent to the bottom side of cap 158, exerting upward force on end portion 154 through the rigid hook of structure 150. This upward force keeps end portion 154 seated in sleeve portion 220, where it restrains connector 150 from swiveling about end portion 152. When the user wishes to open structure 150, pressure from thumb 350 can move cap 158 downward, compressing spring 156 and releasing opposite end portion 154 from sleeve portion 220. Then end portion 152 becomes free to rotate within hole 222 and its counterpart hole 410, and those holes form a pivot axis for rotation of structure 150.

Figure 5:
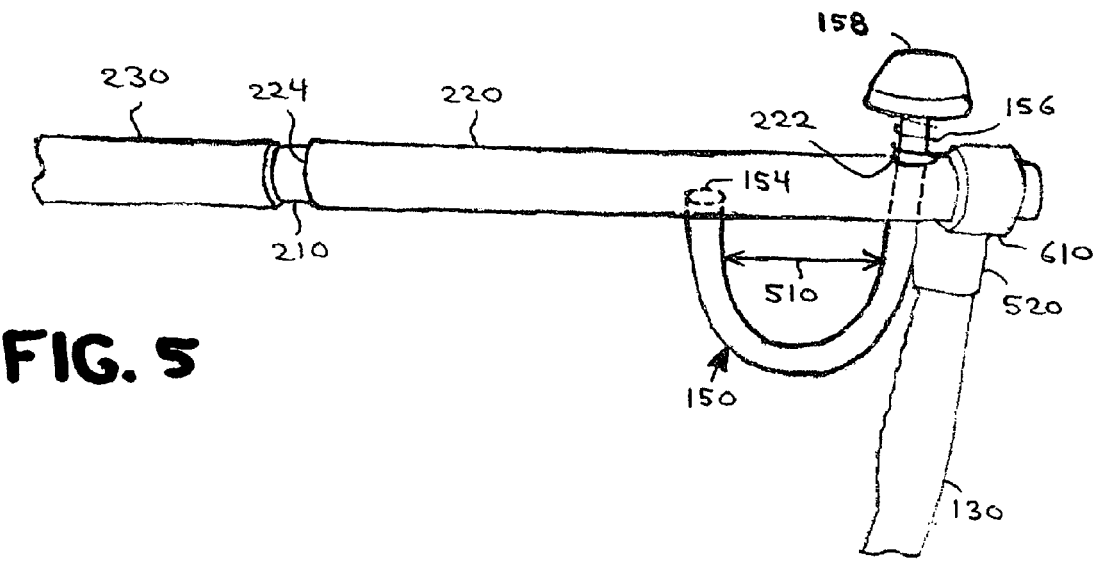
FIG. 5 is a partial view of the bar and strap of FIG. 1.

FIG. 3 illustrates structure 150 partially rotated away from a closed (i.e., non-released) position. FIG. 4 illustrates structure 150 in a fully open position, with end portion 154 free of hole 420 and the plane of the hook of structure 150 perpendicular to the lengthwise axis of sleeve portion 220. FIG. 5 illustrates structure 150 in a fully closed position with its end portion 154 secured in a hollow interior of sleeve portion 220.

When in the open position depicted in FIG. 4, connector 150 can seat receiving tube 144 of breast milk collection device 140 in the arc of its hook. As illustrated in FIG. 3, sleeve portion 220 does not obstruct the open part of the hook of structure 150 when it is in its open position. Receiving tube 144 can snugly fit into the arc of the hook, where connector 150 can then secure it in place by pivoting back to a closed position (FIGS. 1–2). When thumb 350 releases downward pressure on cap 158, spring 156 pushes cap 158 upward, in turn allowing end portion 154 to fit into hole 420, securing both structure 150 and receiving tube 144 to bar 120.

The fit between the hook of structure 150 and receiving tube 144 should be tight enough to keep collection device 140 in a substantially stable orientation, thus facilitating suction at the breast of wearer 110. The fit should be kept loose enough to permit device 140 to oscillate in position somewhat with respect to the breast of wearer 110, an action that device 140 preferably performs to enhance expression of milk. When such oscillation is desired, another advantage of the preferred construction of bar 120 (FIG. 4) becomes apparent. The ability of sleeve portions 220, 230 to rotate independently about rod 210 permits devices 140, 170 to undergo independent oscillatory movements about the lengthwise axis of bar 120.

Figure 6:
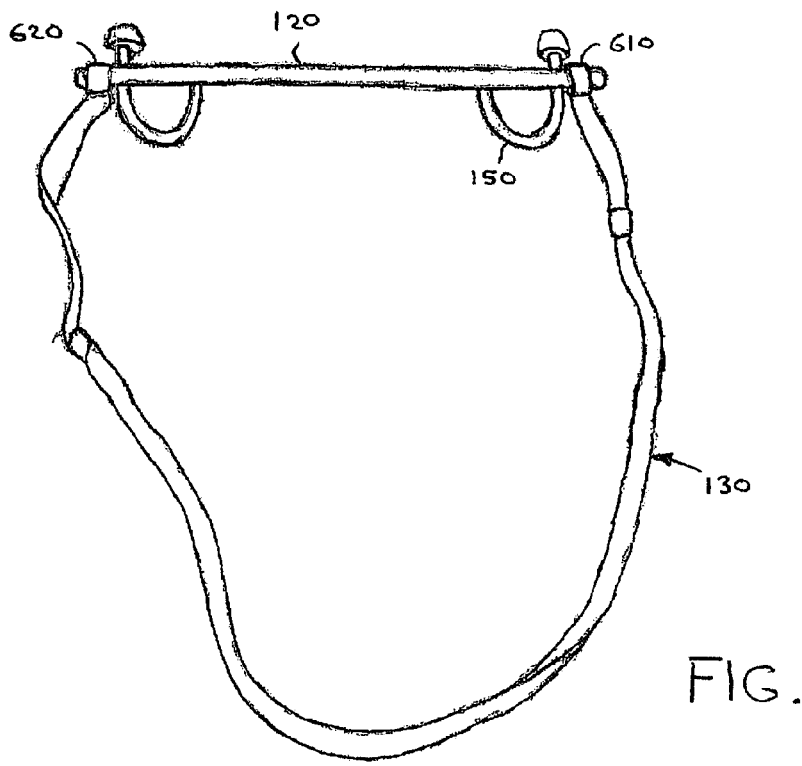
FIG. 6 is a view of the bar and strap of FIG. 1, illustrating how the strap is significantly longer than the bar to permit the strap to fit around a wearer's neck.

Respective points of a strap and bar can connect in any suitable fashion. As may be better understood with reference to FIGS. 5–6, for example, points at ends of exemplary strap 130 connect to respective points of bar 120 with loops 610, 620 of strap material around bar 120. Compression clips secure the end of each loop. As illustrated in FIG. 5, for example, clip 520 secures one end of strap 130 (hidden inside clip 520) to strap material (also hidden) at the beginning of loop 610. Compression clip 520 and its counterpart (not shown), which secures loop 620 (FIG. 6), can be conventionally fabricated from a length of semi-rigid plastic with a U-shaped cross section and ends that touch unless forcibly spread apart.

Sleeve portions 210, 220 of exemplary bar 120 include end caps (e.g., of rubber) that fit inside the hollow of each sleeve, at the ends not receiving rod 210. As illustrated in FIG. 3, for example, end cap 430 fits in one end of sleeve portion 220, while opposite end 224 can receive rod 210. FIG. 4 illustrates another configuration, using end caps 430, 440 that have maximum diameters considerably greater than the outside diameters of sleeve portions 220, 230. As a result, end caps 430, 440 can advantageously prevent end loops of a strap (e.g., strap 130 of FIGS. 5–6) from falling off the ends of bar 120.

Dimensions of a breast milk expression system according to various aspects of the invention can be selected to accommodate expected body shapes and sizes of a population of interest as well as the particular structure employed in such a system. TABLE I below lists exemplary dimensions of system 100 (FIG. 1). These dimensions are not exact or critical, and any precise figures listed in TABLE I are set forth that way to communicate a particular fractional value without the use of fractions.

TABLE I

| Element | Dimension Type | Dimension |
| --- | --- | --- |
| BAR 120 | Length range | 9–16 in. |
| Sleeve portions 220, 230 | Length | 4.5 in. |
| Sleeve portions 220, 230 | Inside diameter | 0.4375 in. |
| Rod 210 | Length | 4.5 in. |
| Rod 210 | Outside diameter | 0.375 in. |
| Sleeve portions & rod 210 | Wall thickness | 0.0345 in. |
| Holes 222, 410, 420 | Diameter | 5 mm |
| End caps 430, 440 | Maximum diameter | 0.75 in. |
| STRAP 130 | Length range | 18–46 in. |
| Padded strap 132 | Length | 16 in. |
| Padded strap 132 | Strap width | 1.5 in. |
| End portions 134, 136 | Length (unlooped) | 14 in. |
| End portions 134, 136 | Strap width | 0.35 in. |
| CONNECTORS 150, 180 | — | — |
| Hook | Arc diameter 510 | 1.1875 in. |
| Hook | Rod outside diameter | 0.1875 in. |
| Washer 153 | Size | "No. 8" |
| Portion 152, hole 222 to washer 153 | Length range | 0.175–0.35 in. |
| Spring 156 | Diameter | 0.28125 in. |
| Spring 156 | Wire thickness | 0.035 in. |
| Spring 156 | Extended length | 0.375 in. |

As illustrated in FIG. 1 with reference to exemplary system 100, a nursing mother can conveniently use a hands-free breast milk expression system according to various aspects of the invention to express milk from both her breasts while keeping her hands free. She can wear the strap around her neck with or without clothing on her torso, and without needing to wear any special bra or other article of clothing. She can easily adjust the system to fit her body, e.g., by first adjusting bar 120 to position breast milk collection devices 140, 170 at the separation of her breasts, then suspending bar 120 from strap 130 around her neck to position devices 140, 170 at the proper distance below her neckline. She can then activate breast milk expression, permitting devices 140, 170 to independently oscillate in motion and thus facilitate expression, while reading a book or engaging in some other activity during the process.

PUBLIC NOTICE REGARDING THE SCOPE OF THE INVENTION AND CLAIMS

The inventor considers various elements of the aspects and methods recited in the claims filed with the application as advantageous, perhaps even critical to certain implementations of the invention. However, the inventor regards no particular element as being "essential," except as set forth expressly in any particular claim.

While the invention has been described in terms of preferred embodiments and generally associated methods, the inventor contemplates that alterations and permutations of the preferred embodiments and methods will become apparent to those skilled in the art upon a reading of the specification and a study of the drawings.

Additional structure can be included, or additional processes performed, while still practicing various aspects of the invention claimed without reference to such structure or processes. For example, breast milk collection devices according to various aspects of the invention can include integrated miniature pumps and thus avoid relying on air hoses connecting to an external pump. As a further example, a bar and strap according to various aspects of the invention can include scales of reference markings to which a wearer can refer when adjusting the bar and strap, e.g. as directed by an interactive Web site that calculates initial bar and strap lengths given a particular bra size. In addition, various structural components, e.g., a bar and strap, can include aesthetically appealing surface coloring or indicia, e.g., nursery ornamentation.

Accordingly, neither the above description of preferred exemplary embodiments nor the abstract defines or constrains the invention. Rather, the issued claims variously define the invention. Each variation of the invention is limited only by the recited limitations of its respective claim, and equivalents thereof, without limitation by other terms not present in the claim.

In addition, aspects of the invention are particularly pointed out in the claims using terminology that the inventor regards as having its broadest reasonable interpretation; the more specific interpretations of 35 U.S.C. § 112(6) are only intended in those instances where the terms "means" or "steps" are actually recited. As one example, the term "substantially rigid" is employed in reference to material that can retain its shape enough to serve its structure's intended purpose when subjected to deforming forces encountered during normal conditions of use. The term does not require that material experience no substantial deformation for it to be considered "substantially rigid."

The words "comprising," "including," and "having" are intended as open-ended terminology, with the same meaning as if the phrase "at least" were appended after each instance thereof. A clause using the term "whereby" merely states the result of the limitations in any claim in which it may appear and does not set forth an additional limitation therein. Both in the claims and in the description above, the conjunction "or" between alternative elements means "and/or," and thus does not imply that the elements are mutually exclusive unless context or a specific statement indicates otherwise.

What is claimed is:

1. Apparatus for breast milk collection comprising:
   (a) a substantially rigid bar;
   (b) a flexible strap significantly longer than the bar and extending from a point at or near one end of the bar to a point at or near another end of the bar; and
   (c) a pair of breast milk collection devices supported by the bar and located at or near opposite ends of the bar.

2. The apparatus of claim 1 wherein the bar comprises a rod and a pair of sleeve portions fitted snugly but adjustably onto the rod.

3. The apparatus of claim 1 wherein the bar is made of metal.

4. A breast-milk collection apparatus comprising:
   (a) a substantially rigid bar having a length that is adjustable over a predetermined adjustment range;
   (b) a flexible strap significantly longer than the bar at the longest point of the adjustment range and extending from a point at or near one end of the bar to a point at or near another end of the bar;
   (c) a pair of cups, each dimensioned and shaped to receive at least a portion of one of a wearer's breasts; and
   (d) a tube extending from, and having a fluid passageway connected to the interior of, each of the cups;
   (e) wherein the tubes are supported by the bar, one at or near each of the opposite ends of the bar.

5. The apparatus of claim 4 further comprising a pair of milk bottles, one of which is connected to each of the tubes.

6. The apparatus of claim 4 wherein the tubes supported by the bar are suspended beneath the bar.

7. The apparatus of claim 4 wherein the tubes supported by the bar are supported with a pair of releasable retainers fastened to the bar and releasably supporting the tubes in proximity to the bar.

8. The apparatus of claim 7 wherein:
   (a) each one of the pair of releasable retaining structures comprises a J-shaped hook and a compression spring;
   (b) the longer end of the hook passes through the bar and the spring; and
   (c) the shorter end of the hook can move in and out of a hole in the bar.

9. The apparatus of claim 4 wherein the bar comprises a rod and a pair of sleeve portions fitted snugly but adjustably onto the rod.

10. The apparatus of claim 1 wherein the strap has a length that is adjustable over a predetermined adjustment range.

11. The apparatus of claim 10 wherein the adjustment ranges for the bar and strap are predetermined to accommodate a significant majority of nursing womens' bodies in a population of interest.

12. A breast-milk collecting apparatus comprising:
   (a) a substantially rigid bar;
   (b) a flexible strap significantly longer than the bar and extending from a point at or near one end of the bar to a point at or near another end of the bar;
   (c) a pair of cups each dimensioned and shaped to receive at least a portion of one of a wearer's breasts;
   (d) a tube extending from, and having a passageway in fluid communication with the interior of, each of the cups; and
   (e) a pair of releasable retainers, one at or near each end of the bar, wherein each retainer is connected to the bar at two points on opposite sides of one of the tubes.

13. The apparatus of claim 12 further comprising a pair of milk bottles, each connected to a respective one of the tubes.

14. The apparatus of claim 12 wherein the bar has a length that is adjustable over a predetermined adjustment range of between about nine inches and about sixteen inches.

15. The apparatus of claim 14 wherein the bar comprises a rod and a pair of sleeve portions fitted snugly but adjustably onto the rod.

16. A method for the collection of breast milk comprising:
   (a) attaching opposite ends of a flexible strap at or near opposite ends of a substantially rigid bar that is significantly shorter than the strap;
   (b) supporting a pair of breast milk collection devices with the bar at or near opposite ends of the bar;
   (c) suspending the strap and bar from a nursing woman's neck, thereby suspending the breast milk collection devices near the nursing woman's breasts to express milk therefrom; and
   d) expressing milk from the nursing woman into the breast milk collection devices.

17. The method of claim 16 further comprising releasably securing each one of the breast milk collection devices to the bar.

18. The method of claim 17 wherein releasably securing comprises:
   (a) providing a pair of releasable retaining structures that each include a J-shaped hook and a compression spring;
   (b) passing the longer end of the hook through the bar and the spring;
   (c) when an open position of one of the retaining structures is desired, moving the shorter end of the hook of the structure out of a hole in the bar and swiveling the hook about its shorter end; and
   (d) when a closed position of one of the retaining structures is desired, moving the shorter end of the hook of the structure into the recess.

19. The method of claim 18 wherein supporting a pair of breast milk collection devices comprises supporting:
   (a) a cup dimensioned and shaped to receive a portion of a human breast around the nipple thereof and including a central opening; and
   (b) a tube having a central opening in fluid communication with the interior of the cup.

* * * * *